United States Patent
Akamatsu et al.

(10) Patent No.: US 10,055,665 B2
(45) Date of Patent: Aug. 21, 2018

(54) ROI SETTING TECHNIQUE FOR IMAGING TEST OF LIVING BODY

(71) Applicants: Foundation for Biomedical Research and Innovation at Kobe, Hyogo (JP); Nihon Medi-Physics Co., Ltd., Tokyo (JP)

(72) Inventors: Go Akamatsu, Hyogo (JP); Michio Senda, Hyogo (JP); Yasuhiko Ikari, Hyogo (JP); Shuya Miki, Tokyo (JP)

(73) Assignees: Nihon Medi-Physics Co., Ltd., Tokyo (JP); Foundation for Biomedical Research and Innovation at Kobe, Hyogo (JP)

( * ) Notice: Subject to any disclaimer, the term of this patent is extended or adjusted under 35 U.S.C. 154(b) by 0 days.

(21) Appl. No.: 15/267,590

(22) Filed: Sep. 16, 2016

(65) Prior Publication Data
US 2017/0083780 A1 Mar. 23, 2017

(30) Foreign Application Priority Data
Sep. 17, 2015 (JP) .................. 2015 184366

(51) Int. Cl.
*G06K 9/32* (2006.01)
*A61B 6/00* (2006.01)
(Continued)

(52) U.S. Cl.
CPC .......... *G06K 9/3233* (2013.01); *A61B 5/0035* (2013.01); *A61B 5/4088* (2013.01);
(Continued)

(58) Field of Classification Search
None
See application file for complete search history.

(56) References Cited

U.S. PATENT DOCUMENTS 8,472,694 B2 * 6/2013 Minoshima ........... G06T 7/0014
382/134
8,693,746 B2 * 4/2014 Ishii ...................... A61B 6/032
382/128

(Continued)

OTHER PUBLICATIONS

Bourgeat, Pierrick, et al., "Comparison of MR-less PiB SUVR quantification methods", Neurobiology of Aging, © 2014 Elsevier Inc., 8 pgs.
Edison, P., et al., "Comparison of MRI based and PET template based approaches in the quantitative analysis of amyloid imaging with PiB-PET", NeuroImage 70, © 2012 Elsevier Inc., 11 pgs.

*Primary Examiner* — Bobbak Safaipour
(74) *Attorney, Agent, or Firm* — Harrington & Smith

(57) ABSTRACT

In imaging analysis of a living body, a Region Of Interest (ROI) is set on the basis of the state of radiopharmaceutical accumulation. An example for setting an ROI includes: performing first transformation for anatomically standardizing, with the use of a positive template, a nuclear medicine image acquired by applying a radiopharmaceutical to a subject; performing second transformation for anatomically standardizing, with the use of a negative template, the nuclear medicine image; calculating a degree of similarity between a first anatomical standardization image acquired by the first transformation and the positive template; calculating a degree of similarity between a second anatomical standardization image acquired by the second transformation and the negative template; and applying, to an ROI template, inverse transformation of the first transformation or the second transformation, whichever has the higher of the calculated degrees of similarity, in order to set the ROI.

16 Claims, 10 Drawing Sheets

(51) Int. Cl.

| | |
|---|---|
| *G06K 9/46* | (2006.01) |
| *G06T 7/00* | (2017.01) |
| *G06K 9/62* | (2006.01) |
| *G06T 11/00* | (2006.01) |
| *A61B 6/03* | (2006.01) |
| *A61B 5/00* | (2006.01) |
| *G06T 7/33* | (2017.01) |
| *A61B 5/055* | (2006.01) |
| *G01R 33/48* | (2006.01) |

(52) U.S. Cl.
CPC .......... *A61B 5/7425* (2013.01); *A61B 5/7485* (2013.01); *A61B 6/037* (2013.01); *A61B 6/469* (2013.01); *A61B 6/501* (2013.01); *A61B 6/5211* (2013.01); *G06K 9/6255* (2013.01); *G06T 7/0012* (2013.01); *G06T 7/337* (2017.01); *G06T 11/006* (2013.01); *A61B 5/055* (2013.01); *A61B 5/4082* (2013.01); *A61B 6/461* (2013.01); *A61B 2576/026* (2013.01); *G01R 33/481* (2013.01); *G06T 2207/10088* (2013.01); *G06T 2207/10104* (2013.01); *G06T 2207/20128* (2013.01); *G06T 2207/30016* (2013.01)

(56) References Cited

U.S. PATENT DOCUMENTS

| | | | |
|---|---|---|---|
| 9,788,784 B2* | 10/2017 | Reiman | A61B 5/4848 |
| 2009/0290765 A1* | 11/2009 | Ishii | A61B 5/055 |
| | | | 382/128 |
| 2011/0105881 A1* | 5/2011 | Kakimoto | G06T 7/0012 |
| | | | 600/407 |
| 2011/0188719 A1* | 8/2011 | Ishii | A61B 6/032 |
| | | | 382/128 |
| 2013/0116540 A1* | 5/2013 | Li | A61B 5/055 |
| | | | 600/410 |
| 2013/0304683 A1* | 11/2013 | Lo | G06N 3/06 |
| | | | 706/20 |
| 2014/0086836 A1* | 3/2014 | Burnham | G01N 33/6896 |
| | | | 424/1.81 |
| 2014/0307936 A1* | 10/2014 | Dore | G06T 7/0014 |
| | | | 382/131 |
| 2015/0080703 A1* | 3/2015 | Reiman | A61B 5/4848 |
| | | | 600/409 |
| 2016/0245828 A1* | 8/2016 | Roberts | A61B 5/4076 |
| 2016/0260216 A1* | 9/2016 | Wu | G06T 7/0016 |
| 2017/0017393 A1* | 1/2017 | Luo | G06F 3/04886 |
| 2017/0186155 A1* | 6/2017 | Wenzel | G06T 7/0012 |
| 2018/0045798 A1* | 2/2018 | Yokosawa | A61B 5/0037 |

* cited by examiner

EXAMPLE OF POSITIVE TEMPLATE    EXAMPLE OF NEGATIVE TEMPLATE

ROI SETTING TECHNIQUE FOR IMAGING TEST OF LIVING BODY

TECHNICAL FIELD

The present application discloses an invention for ROI setting in imaging tests of a living body and discloses, for example, an ROI setting method and a method for producing a template that can be used for ROI setting.

BACKGROUND ART

Accumulation of amyloid β-protein in the cerebral cortex is recognized as being related to Alzheimer's disease, and quantitative evaluation of amyloid accumulation is being studied for differential diagnosis of, and determination of therapeutic effects on, Alzheimer's disease.

Non Patent Literature 1, which presents results of such a test, discloses a method that uses a so-called adaptive atlas. An adaptive atlas is generated as follows. A plurality of subjects are made to undergo PET with the use of $^{11}$C-PiB as an amyloid marker to acquire a PiB image (PET image acquired by the use of $^{11}$C-PiB) of each of the subjects. After the acquired PiB images have been anatomically standardized on the basis of MRI images, they are classified into two groups according to the magnitude of the SUVR in the cerebral neocortex area, so that a positive atlas is generated from one group and a negative atlas is generated from the other group. Then, when amyloid deposition is to be studied from a PiB image of a new subject, an adaptive atlas is first generated for that PiB image by linear coupling between the positive atlas and the negative atlas. The method is characterized in that weighting for this linear coupling is determined individually for each PiB image to be studied. Non Patent Literature 1 discloses that this individually determined adaptive atlas is used to anatomically standardize the corresponding PiB image, and AAL parcellation, which is an existing brain atlas, is then used to extract the cerebral neocortex area and calculate its SUVR.

Non Patent Literature 1 also discloses a method that uses a so-called mean atlas. This method is also described in detail in Non Patent Literature 2. First, a mean atlas is generated merely by position-adjusting and overlaying PiB images from a plurality of subjects. Thereafter, the PiB image to be studied is position-adjusted with respect to this atlas, and the cerebral neocortex area is extracted by the use of AAL parcellation, which is an existing brain atlas, to calculate its SUVR.

CITATION LIST

Non Patent Literature (NPL)

[NPL 1] Bourgeat et al.—2019—Comparison of MR-less PiB SUVR quantification methods
[NPL 2] Edison et al.—2013—Comparison of MRI based and PET template based approaches in the quantitative analysis of amyloid imaging with PIB-PET

SUMMARY OF INVENTION

Currently, amyloid accumulation is quantitatively evaluated mainly by having a subject undergo PET by the use of a radiopharmaceutical that is accumulated in amyloid β-protein, having the same subject undergo MRI, anatomically standardizing the PET image representing the state of amyloid deposition by the use of the MRI image, and selecting a particular area to examine the pixel values in the area.

Currently, quantitative evaluation of amyloid deposition is conducted only at the clinical study level and is no longer used as a common medical technique. One of the reasons is that not only PET but also MRI is necessary in order to make a quantitative evaluation of amyloid deposition. MRI images are necessary in order to anatomically standardize PET images and to set the area to be evaluated (region of interest (ROI)), as described above. It is burdensome to equip many medical organizations with not only a PET apparatus but also an MRI apparatus in terms of cost and maintenance. Furthermore, an MRI test, in addition to a PET test, is also very burdensome to persons who need to have examinations. This is because dementia patients are required to lie still for a longer period of time in order to acquire an MRI image, which is a difficult task to dementia patients. For this reason, there is a demand for quantitative evaluation of amyloid deposition that is possible with a PET test alone.

Furthermore, existing methods for evaluating amyloid accumulation use an existing brain atlas, like AAL parcellation, to extract an area in which the state of amyloid deposition is to be studied. Although these existing brain atlases are regarded as faithfully representing the anatomical structure of the brain, they are not a map generated on the basis of the state of accumulation of radiopharmaceuticals. Because of this, it may not be optimal in a PET test to use an existing brain atlas to determine the area to be analyzed (ROI).

Furthermore, in existing methods, an ROI has been set and the pixel values, the SUVR, and so forth of the ROI have been examined only after the original amyloid image has been anatomically standardized (i.e., has been reshaped). Anatomical standardization, however, leads to a change in the pixel value. Therefore, there has been a demand for setting an ROI on the original image at all times when possible.

In order to solve at least one of the above-described problems, the following method will be disclosed. This method is a method for setting an ROI for an imaging test of a living body and includes:

performing first transformation for anatomically standardizing, with the use of a positive template, a nuclear medicine image acquired by applying a radiopharmaceutical to a subject;

performing second transformation for anatomically standardizing the nuclear medicine image with the use of a negative template;

calculating a degree of similarity between a first anatomical standardization image acquired by the first transformation and the positive template;

calculating a degree of similarity between a second anatomical standardization image acquired by the second transformation and the negative template; and applying, to an ROI template, inverse transformation of the first transformation or the second transformation, whichever has the higher of the calculated degrees of similarity, in order to set the ROI.

Depending on the embodiment, the above-described positive template may be generated from nuclear medicine images of a plurality of subjects having a disease for which a nuclear medicine imaging test is conducted with the above-described radiopharmaceutical.

Depending on the embodiment, the above-described negative template may be generated from nuclear medicine images of a plurality of subjects not having the above-described disease.

Depending on the embodiment, the above-described ROI template may be generated on the basis of a difference between the above-described positive template and the above-described negative template.

According to the above-described method, an ROI for examining the accumulation of the relevant radiopharmaceutical can be set appropriately because an ROI is set using a template generated with a radiopharmaceutical actually used in a nuclear medicine test. In particular, an ROI can be set appropriately by using three types of templates, including the positive template, the negative template, and the ROI template, as described above.

Furthermore, it becomes possible to directly set an ROI on the original image to be examined because an ROI used for an imaging test is set by applying inverse transformation of anatomical standardization to the ROI template. Therefore, the pixel values of an ROI can be analyzed without changing the pixel values of the original image.

In addition, the above-described method does not require MRI to be performed in order to set an ROT on a nuclear medicine image. Therefore, the equipment burden in medical facilities and the patient examination burden can be suppressed.

Test data acquired when the above-described method was applied to amyloid imaging will be introduced later. An ROI that is set by the above-described method would be more favorable compared with an ROI that is set by a conventional method using MRI and an existing brain atlas in terms of stability and partial volume effect. Furthermore, when it was determined whether Alzheimer's disease existed on the basis of ROIs that were set by the above-described method, the result demonstrated that a discriminating capability at the same level as that of visual inspection by richly-experienced physicians was achieved.

Note that an ROI may be set by replacing the processing of "applying, to the ROI template, inverse transformation of the first transformation or the second transformation, whichever has the higher of the calculated degrees of similarity," with the processing of "applying the ROI template to the first anatomical standardization image or the second anatomical standardization image, whichever has the higher of the calculated degrees of similarity."

The above-described method is characterized in that three types of templates, including the positive template, negative template, and ROI template, are used, and the present application also discloses a method for producing these templates. In a preferable embodiment, this method includes:

accessing a plurality of first types of nuclear medicine images, wherein the plurality of first types of nuclear medicine images are images acquired by administering a radiopharmaceutical to different subjects and performing nuclear medical measurement for each of them, and the subjects are ones having a disease which can be a target of a nuclear medicine imaging test;

applying anatomical standardization and pixel value normalization to the plurality of first types of nuclear medicine images and performing arithmetic averaging to acquire a positive template;

accessing a plurality of second types of nuclear medicine images, wherein the plurality of second types of nuclear medicine images are images acquired by administering a radiopharmaceutical to different subjects and performing a nuclear medical measurement for each of them, and the subjects are subjects not having the disease;

applying anatomical standardization and pixel value normalization to the plurality of second types of nuclear medicine images and performing arithmetic averaging to acquire a negative template; and acquiring the ROI template by taking a difference between pixels extracted from the positive template on the basis of a predetermined pixel value threshold (e.g., pixels that have a pixel value equal to or above a predetermined threshold and that are extracted from the positive template) and pixels extracted from the negative template on the basis of a predetermined pixel value threshold (e.g., pixels that have a pixel value equal to or above a predetermined threshold and that are extracted from the negative template).

The present invention has been made to appropriately set an area to be analyzed with PET alone, i.e., without requiring MRI, in amyloid imaging for differential diagnosis of, and determination of therapeutic effects on, Alzheimer's disease. However, the resultant present invention has become capable of being widely used not only for this purpose but also for nuclear medicine diagnosis. The present invention can be widely used to set an area to be analyzed on an image of a living body, particularly in a field where the presence of a disease can be identified according to the accumulation pattern of a radiopharmaceutical.

Therefore, a "living body" in the above-described method can be, but is not limited to, for example, the human brain cortex and can also be, for example, the human corpus striatum and hippocampus.

In addition, a "radiopharmaceutical" in the above-described method can be, but is not limited to, for example, a radiopharmaceutical for amyloid imaging, such as Pittsburgh Compound-B labeled with $^{11}C$ ($^{11}C$-PIB ([N-methyl-$^{11}C$]2-(4'-methylaminophenyl)-6-hydroxybenzothiazole)) and a pharmaceutical drug labeled with $^{18}F$ ($^{18}F$-florbetapir, $^{18}F$-Flutemetamol, etc.), and can also be, for example, $^{18}F$-FDOPA, $^{11}C$-Raclopride, $^{123}I$-FP-CIT, and $^{123}I$-IMP.

Furthermore, an "imaging test" in the above-described method can include, for example, an MRI test and a nuclear medicine imaging test. In addition, a "nuclear medicine imaging test" can be, for example, a PET test and can be an amyloid imaging test for examining, for example, amyloid deposition. A "nuclear medicine image" can be, for example, a PET image and can be an amyloid image depicting deposition of, for example, amyloid. A "nuclear medicine imaging test" and a "nuclear medicine image" can be a SPECT test and a SPECT image, depending on the embodiment.

Furthermore, a "disease applicable to a nuclear medicine imaging test" in the above-described method can be, but is not limited to, for example, Alzheimer's disease, and can also be, for example, dementia with Lewy bodies and Parkinson's disease.

Preferable embodiments of the present invention include: an apparatus configured to carry out the above-described method; a computer program configured to cause an apparatus to perform the above-described method when executed by a processing means such as a CPU; and so forth.

Some of the embodiments according to the present invention that are considered to be preferable at the present time are identified in the claims. However, structures identified in these claims do not include all the new technical ideas disclosed in the description and drawings of the present application. The applicants claim to have the rights to be granted a patent for all the new technical ideas disclosed in the description and drawings of the present application, whether they are described or not in the current claims.

DETAILED DESCRIPTION OF PREFERRED EMBODIMENTS

Technical ideas disclosed in the present application will now be described in more detail by way of preferable embodiments with reference to the appended drawings. Technical ideas disclosed in the present application have two aspects when roughly divided. One relates to producing a template set used to determine an ROI for an imaging test of a living body, and the other relates to setting an ROI for an imaging test of a living body by the use of that template set. First, the former aspect will be described.

Figure 1:
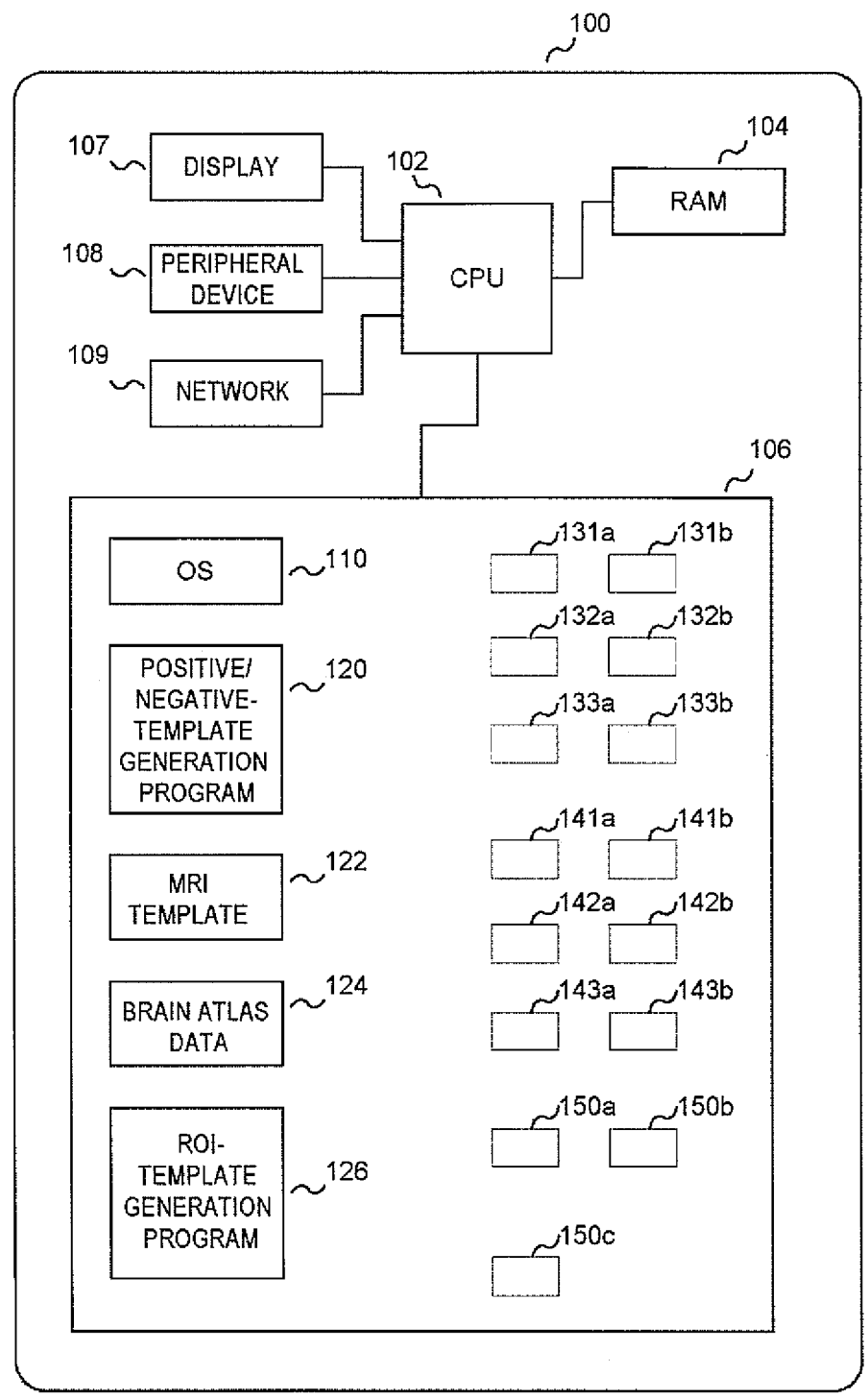
FIG. 1 is a diagram depicting a hardware configuration of a system for producing a template set used to determine an ROI for an imaging test of a living body.

FIG. 1 is a diagram depicting main structures of a system 100, which is an example of hardware for producing the above-described template set. As depicted in FIG. 1, the system 100 is identical to a general computer in terms of hardware and can be provided with a CPU 102, a main storage device 104, a large-capacity storage device 106, a display interface 107, a peripheral device interface 108, a network interface 109, and so forth. As with a general computer, a fast RAM (random access memory) can be used as the main storage device 104, and a less expensive and large-capacity hard disk, an SSD, and so forth can be used as the large-capacity storage device 106. A display for displaying information can be connected to the system 100, and this display is connected via the display interface 107. In addition, a user interface such as a keyboard, a mouse, and a touch panel can be connected to the system 100, and this user interface is connected via the peripheral device interface 108. The network interface 109 can be used to connect to another computer or the Internet via a network.

The large-capacity storage device 106 can store: an operating system (OS) 110; programs 120 and 126 provided with an instruction for producing the above-described template set; and an MRI template 122, brain atlas data 124, and so forth used by these programs. The most fundamental function of the system 100 is provided as a result of the OS 110 being executed by the CPU 102. Furthermore, characteristic processing for producing the above-described template set is provided as a result of at least some of the program instructions included in the programs 120 and 126 being executed by the CPU 102. As is well known, various implementation forms of a program are available, and all those variations are encompassed in the scope of the invention disclosed in the present application.

The large-capacity storage device 106 can further store: PET image data 131a, 132a, . . . , 141a, 142a, . . . used to generate the above-described template set; corresponding MRI image data 131b, 132b, . . . , 141b, 142b, . . . ; a positive template 150a, a negative template 150b, and an ROI template 150c included in the above-described template set; and so forth.

In addition to the components depicted in FIG. 1, the system 100 can be provided with structures identical to devices included in a normal computer system, such as a power supply and a cooling device. As implementation forms of a computer system, various forms using a wide variety of techniques are well known, including distribution and virtualization of storage devices, use of a plurality of CPUs, CPU virtualization, use of a processor specialized for specific processing, such as a DSP, implementation of particular processing into hardware combined with a CPU, and so forth. The invention disclosed in the present application may be installed on any form of computer system, and its scope is not limited by the form of the computer system. Technical ideas disclosed in this description can be generally embodied as: (1) a program provided with an instruction configured to allow an apparatus or a system provided with a processing means to accomplish various types of processing described in this description when the program is executed by the processing means; (2) an operating method of an apparatus or a system achieved as a result of the relevant processing means executing the relevant program; (3) an apparatus or a system provided with the relevant program and a processing means configured to execute the relevant program; and so forth. As described above, part of software processing may be implemented in hardware.

Furthermore, it should be noted that when the system 100 is manufactured, sold, and started up, the data 131a, 132a, 131b, 132b, and so forth are not often stored in the large-capacity storage device 106. These data may be data that are transferred from an external device to the system 100 via, for example, the peripheral device interface 108 and the network interface 109. Depending on the embodiment, the data (templates) 150a to 150c may be ones generated through the execution of the programs 120 and 126 by the CPU 102. In addition, depending on the implementation of the programs 120 and 126 and the OS 110, at least one of the PET image data, the MRI image data, the templates, and so forth may not be stored in the large-capacity storage device 106 but may be stored only in the main storage device 104. It should be noted that the scope of the invention disclosed in the present application is not limited by the presence of these data.

Figure 2:
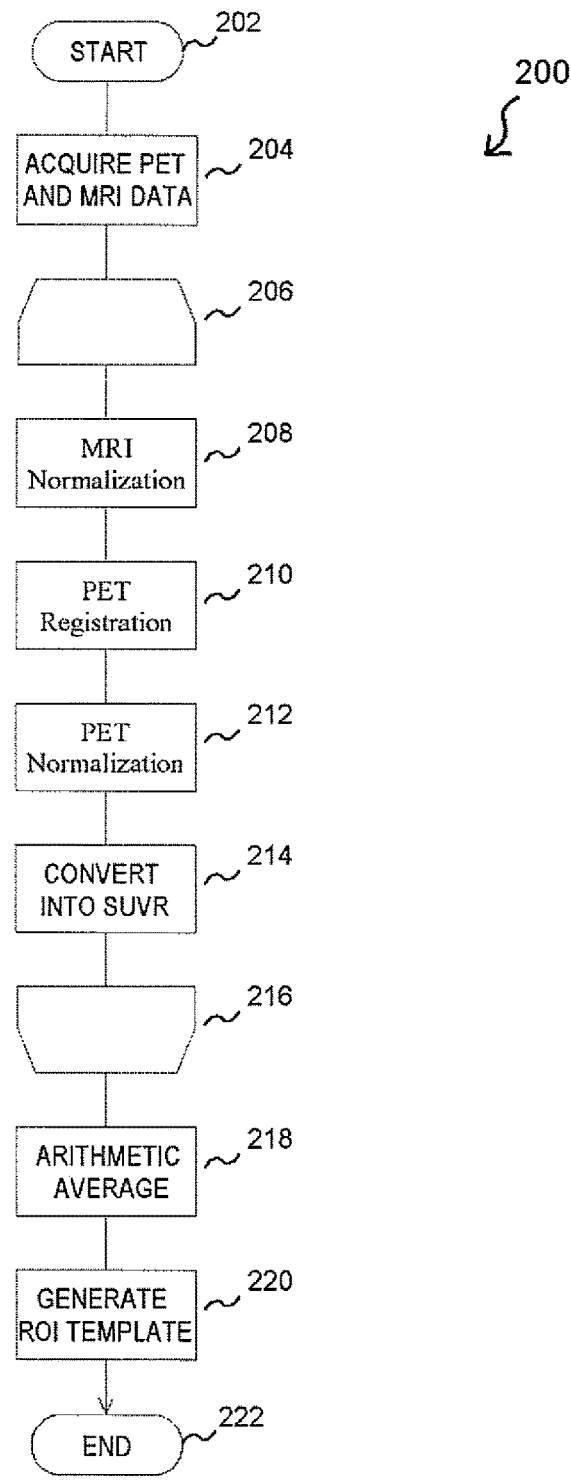
FIG. 2 is a diagram depicting a flow of an embodiment for producing a template set used to determine an ROI for an imaging test of a living body.

Next, the flow of a method 200 for producing a template set used to determine an ROI for an imaging test of a living body will be described with reference to the flowchart of FIG. 2. This template set is composed of three templates including: a positive template generated from nuclear medicine image data of a plurality of subjects having a disease for which the relevant imaging test is conducted; a negative template generated from nuclear medicine image data of a plurality of subjects who do not have the relevant disease; and an ROI template serving as an ROI template used for an imaging test. As one example, a template set generated by the method 200 may be one used for an amyloid imaging test that is conducted for the purpose of discrimination of, and determination of therapeutic effects on, Alzheimer's disease. This template set makes it possible to automatically set an appropriate ROI for analysis in examining, for example, an amyloid image.

Step 202 indicates the start of the method 200. In step 204, data from which templates originate is acquired. Here, several subjects who are known to have no Alzheimer's disease and several subjects who are known to have Alzheimer's disease are collected. To prevent the result from being affected by data of particular individuals, it is preferable that as many patients as possible be collected, including both patients who have and patients who do not have Alzheimer's disease. Then, each of these subjects is made to undergo PET with a radiopharmaceutical (e.g., $^{11}$C-PiB, $^{18}$F-Flutemetamol) used for amyloid imaging to generate PET images. Along with PET, each of these subjects is made to undergo MRI to generate MRI images. The generated image data are stored in an appropriate storage means.

In the present example, the generated PET image data and MRI image data are stored in the auxiliary storage device 106. In FIG. 1, reference signs 131a and 131b denote PET image data and MRI image data, respectively, of a first AD subject (a subject having Alzheimer's disease), reference signs 132a and 132b denote PET image data and MRI image data, respectively, of a second AD subject, and reference signs 133a and 133b denote PET image data and MRI image data, respectively, of a third AD subject. Reference signs 141a and 141b denote PET image data and MRI image data, respectively, of a first non-AD subject (a subject not having Alzheimer's disease), reference signs 142a and 142b denote PET image data and MRI image data, respectively, of a second non-AD subject, and reference signs 143a and 143b denote PET image data and MRI image data, respectively, of a third non-AD subject. Although FIG. 1 depicts PET image data and MRI image data of only three AD subjects and three non-AD subjects, more subjects may be used when templates are to be actually generated, and that is favorable. This is because if the number of subjects (i.e., the number of data items) is small, the impact of data for a particular subject on the finally generated templates is enormous.

In the loop indicated by reference signs 206-216, processing in steps 208-214 is applied to the PET image data and the MRI image data of subjects for whom data acquisition has been carried out in step 204. The purpose of the processing in steps 208-214 is to move and reshape the PET image data of all subjects for whom data acquisition has been carried out in step 204, so that the positions, shapes, and sizes will match, thereby allowing arithmetic averaging of these PET image data to be carried out in step 218. When image data of each of the subjects is processed in each iteration of the loop 206-216 and processing of data of all subjects for whom data acquisition has been performed in step 204 finishes, the loop is exited. Depending on the embodiment, the processing of loop 206-216 is executed by the apparatus 100 as a result of at least some of the program instructions included in the positive/negative-template generation program 120 (refer to FIG. 1) being executed by the CPU 102. This also applies to processing in step 218.

In step 208, the MRI image data of a particular subject (hereinafter, the image data 131b is used as an example) is anatomically standardized so as to match an appropriate MRI template. In short, the position, the shape, and the size of the relevant MRI image data are moved and reshaped so as to match the relevant MRI template. For this MRI template, for example, the MNI (Montreal Neurological Institute) T1 template, which is often used in the technical field of the present application, may be used. In order to carry out this anatomical standardization processing, the CPU 102 may load the MRI template 122, which is the MNI T1 template, from the auxiliary storage device 106 according to at least some of the program instructions of the positive/negative-template generation program 120. Alternatively, a program that can execute this standardization processing is already available, and a program, like PMOD (manufactured by PMOD Technologies Ltd) and SPM (http://www.fil.ion.ucl.ac.uk/spm/), can be used. Depending on the embodiment, the positive/negative-template generation program 120 may be made by using such an existing program. When standardization processing is successful, at least some of the program instructions of the program 120 operate the CPU 102 so as to store transformation information required for the standardization of the image data 131b. In many cases, these pieces of transformation information can be represented in a matrix shape and can be data containing information such as a rotational angle and a local displacement of the data 131b.

In step 210, registration (image position adjustment) of the PET image data corresponding to the MRI image data processed in step 208 to the relevant MRI image data is carried out. In short, if the MRI image data processed in step 208 is, for example, the image data 131b of FIG. 1, the PET image data 131a is subjected to registration to the image data 131b. In other words, the PET image data 131a is moved so that its position, shape, and size match those of the MRI image data 131b. A program that can execute such registration is already available, and a program, such as the above-described PMOD and SPM, can be used. Depending on the embodiment, the positive/negative-template generation program 120 may be made using such an existing program.

In step 212, transformation information (e.g., a matrix) for the anatomical standardization acquired in step 208 is applied to the PET image data (e.g., the image data 131a) subjected to registration to the MRI image in step 210. By doing so, the position, the shape, and the size of the image of a living body shown in the PET image data (e.g., the image data 131a) match those of the image of a living body shown in the MRI template 122.

In step 214, the pixel values of the PET image data transformed in step 212 are normalized. In order to carry out this normalization processing, the CPU 102 loads the brain atlas data 124 from the auxiliary storage device 106 according to at least some of the program instructions of the positive/negative-template generation program 120 and uses it to extract an area serving as a reference for normalization from the PET image data that has been anatomically standardized in step 212. As brain atlas data used for this processing, brain atlas data normally used in the technical field of the present application can be used, and, for example, the AAL (Automatic-anatomical-labeling) ROI can be used. It is preferable that position/shape adjustment between this brain atlas data 124 and the MRI template 122 have been made in advance. In the case of amyloid imaging, an area serving as a reference for normalization can be, for example, the cerebellum. This is because the amount of accumulation of a radiopharmaceutical used for amyloid imaging in the cerebellum does not depend very much on the presence of Alzheimer's disease. For the same reason, the pons can be set as a reference area.

If the cerebellum is to be used as a reference area, pixels of an area the same as the area corresponding to the cerebellum in the brain atlas data 124 are extracted from the PET image data that has been anatomically standardized in step 212 to calculate the average of the pixel values of those pixels. Then, normalization is carried out by dividing the pixel value of each pixel of the PET image data by this average. Note that the pixel values normalized by such processing are normally referred to as an SUV (Standardized Uptake Value) or an SUVR (Standardized Uptake Value Ratio) in the technical field of the present application.

When the loop denoted by reference signs 206-216 is exited, the positions, shapes, and sizes of the images of living bodies of all PET image data processed in this loop are made identical to one another, and also each pixel value is transformed into an SUVR.

In step 218, of all the PET image data processed in the above-described loop, all data originating from the AD subjects are subjected to arithmetic averaging. By doing so, the above-described positive template is generated. In addition, of all the PET image data processed in the loop denoted by reference signs 206-216, all data originating the non-AD subjects are also subjected to arithmetic averaging. By doing so, the above-described negative template is generated. These templates may be saved in the auxiliary storage device 106 as the positive template 150a and the negative template 150b, respectively.

Figure 3:
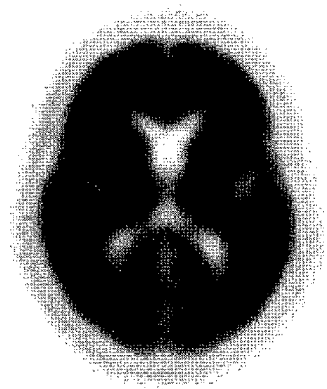
FIG. 3 is a diagram depicting one example of a positive template and one example of a negative template.
Figure 3:
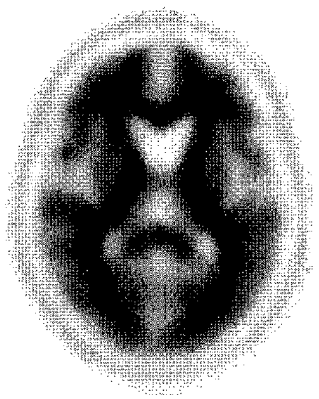

FIG. 3 shows one example of the generated positive template and one example of the negative template. This positive template was generated using amyloid images of eleven AD subjects, and the negative template was generated using amyloid images of eight non-AD subjects.

In step 220, the above-described ROI template is generated by taking the difference between the positive template and the negative template generated in the previous step. Depending on the embodiment, the processing in step 220 may be processing carried out by the apparatus 100 as a result of at least some of the program instructions included in the ROI-template generation program 126 (refer to FIG. 1) being executed by the CPU 102. The generated ROI template may be saved in the auxiliary storage device 106 as the ROI template 150c.

Figure 4A:
FIG. 4A illustrates an example of a positive template that has been subjected to cutoff processing using a threshold.
Figure 4B:
FIG. 4B illustrates an example of a negative template that has been subjected to cutoff processing using a threshold.
Figure 4C:
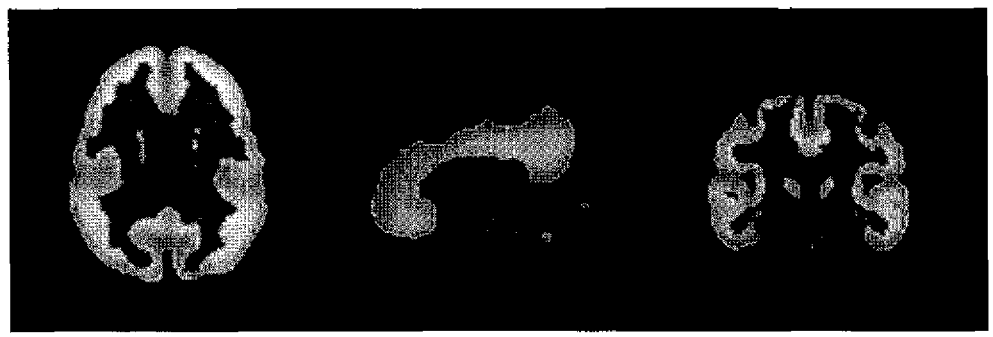
FIG. 4C illustrates an ROI template generated on the basis of the differences between the positive and negative templates.

Depending on the embodiment, the difference may be taken after processing as described below has been applied to the positive template and the negative template, rather than taking a mere difference between these templates. First, for the positive template, only pixel values (SUVR) that are equal to or above a predetermined threshold are left, and all the other pixels are set to a pixel value of 0 or NULL. FIG. 4A shows some examples of image data generated by applying such processing to the positive template. Similarly, also for the negative template, only pixel values (SUVR) that are equal to or above a predetermined threshold are left, and all the other pixels are set to a pixel value of 0 or NULL. FIG. 4B shows some examples of image data generated by applying such processing to the negative template. Finally, the difference between these data is taken, and furthermore, the outlines of clusters formed by pixels having pixel values equal to or above a certain threshold are extracted to generate the ROI template. FIG. 4C shows some examples of the ROI template generated through such processing. Here, in a preferable aspect, the pixel values of the pixels left as a result of the above-described processing (cutoff processing using a threshold) are set to the same value for each of the positive template and the negative template. By carrying out such processing, portions in which pixel values overlap between the positive template and the negative template are always set to a value of 0, allowing a better ROI template to be generated.

As described above, the present inventors have found that producing an ROI template using pixels having SUVRs equal to or above a certain value brings about a beneficial effect on quantitative analysis of a nuclear medicine image. The present inventors have also found that, in the case of amyloid imaging, about 1.7 is suitable as this threshold for both the positive template and the negative template. Note that this threshold is not constant but may be different between the positive template and the negative template. The optimal threshold may change depending on the radiopharmaceutical and the nuclear medicine imaging apparatus to be used, and individual facilities may explore their own optimal values.

Figure 4D:
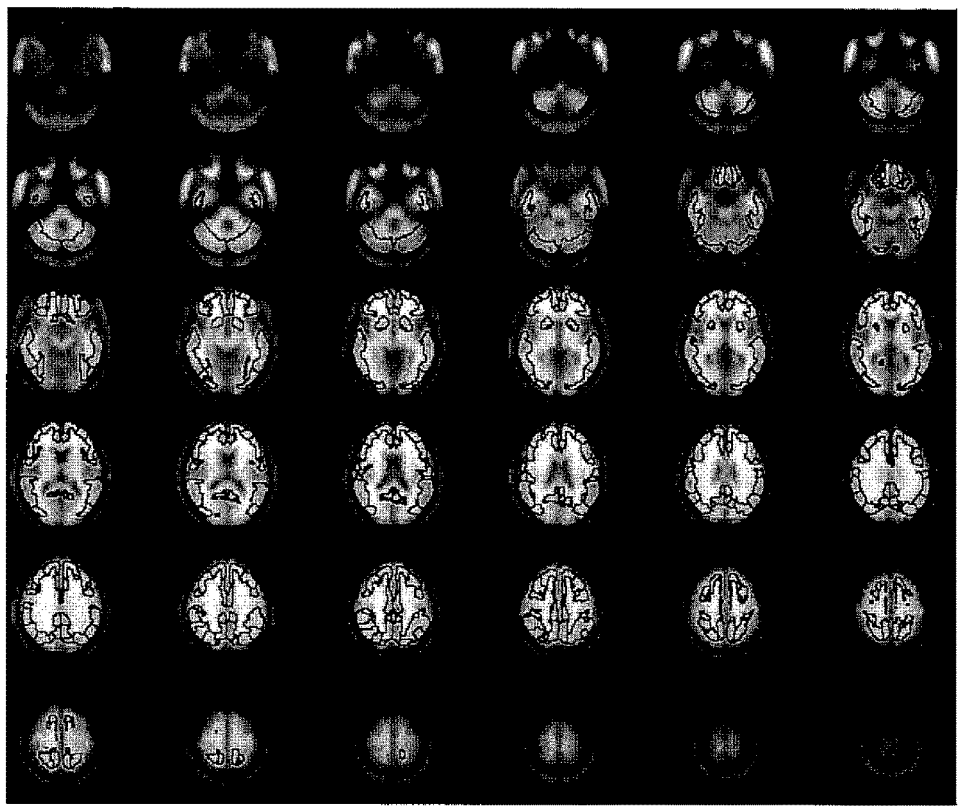
FIG. 4D is a diagram depicting examples of ROI templates generated in an introduced embodiment.

FIG. 4D shows examples of the ROI template generated in step 220. The areas enclosed by a black solid line on each cross-sectional image represent ROIs on the relevant cross-sectional image. This ROI template results from applying the above-described cutoff processing described with reference to FIGS. 4A and 4B to the positive template and to the negative template illustrated in FIG. 3 and then taking the difference between the positive and negative templates.

Because this ROI template is a template generated using an amyloid image obtained using a radiopharmaceutical actually used in an amyloid imaging test, an ROI that has been set on an amyloid image using this template is considered to more directly reflect the state of amyloid accumulation than a conventional ROI that is set using an anatomical brain atlas. Furthermore, because this ROI template is a template generated using PET images, it is considered that it reflects the way the PET apparatus detects radiation. In this respect, the way of detecting radiation is not taken into account at all in the case of a conventional ROI that is set using an anatomical brain atlas. Because of this, a more appropriate ROI can be set using the above-described ROI template in an amyloid imaging test than using a conventional method for setting an ROI on the basis of an anatomical brain atlas.

Furthermore, considering that the above-described ROI template more directly reflects the state of amyloid accumulation than a conventional template based on an anatomical brain atlas, this ROI template will also be helpful in setting an ROI on an MRI image. This is because a change in the morphology can be observed by identifying the area that may have abnormal amyloid accumulation. Therefore, the ROI template according to the present invention is effective not only for ROI setting in a nuclear medicine imaging test but also for a morphological imaging test such as MRI and CT.

Although the above-described ROI template is one generated by way of example of a PiB image, a similar ROI template can also be generated for nuclear medicine images using another radiopharmaceutical. In particular, in a case where the accumulation pattern of a radiopharmaceutical distinctly differs depending on the presence of a disease, and there is an area in which the accumulation pattern does not change depending on the presence of a disease, a similar ROI template can be generated. Such an ROI template makes it possible to set not only an ROI directly based on the state of radiopharmaceutical accumulation but also an ROI taking into account the way the nuclear medicine examination apparatus used detects radiation, leading to a more appropriate ROI compared with a conventional method for setting an ROI merely using an anatomical brain atlas.

Incidentally, it has not been described what the positive template and the negative template, which are two other templates generated by the method 200, are used for. These are templates that can be used when an ROI is to be set on individual images of a living body using the ROI template. A method for setting an ROI on an image of a living body, which is a second aspect of the technical ideas disclosed in the present application, will be described below, along with how to use the positive template and the negative template.

Figure 5:
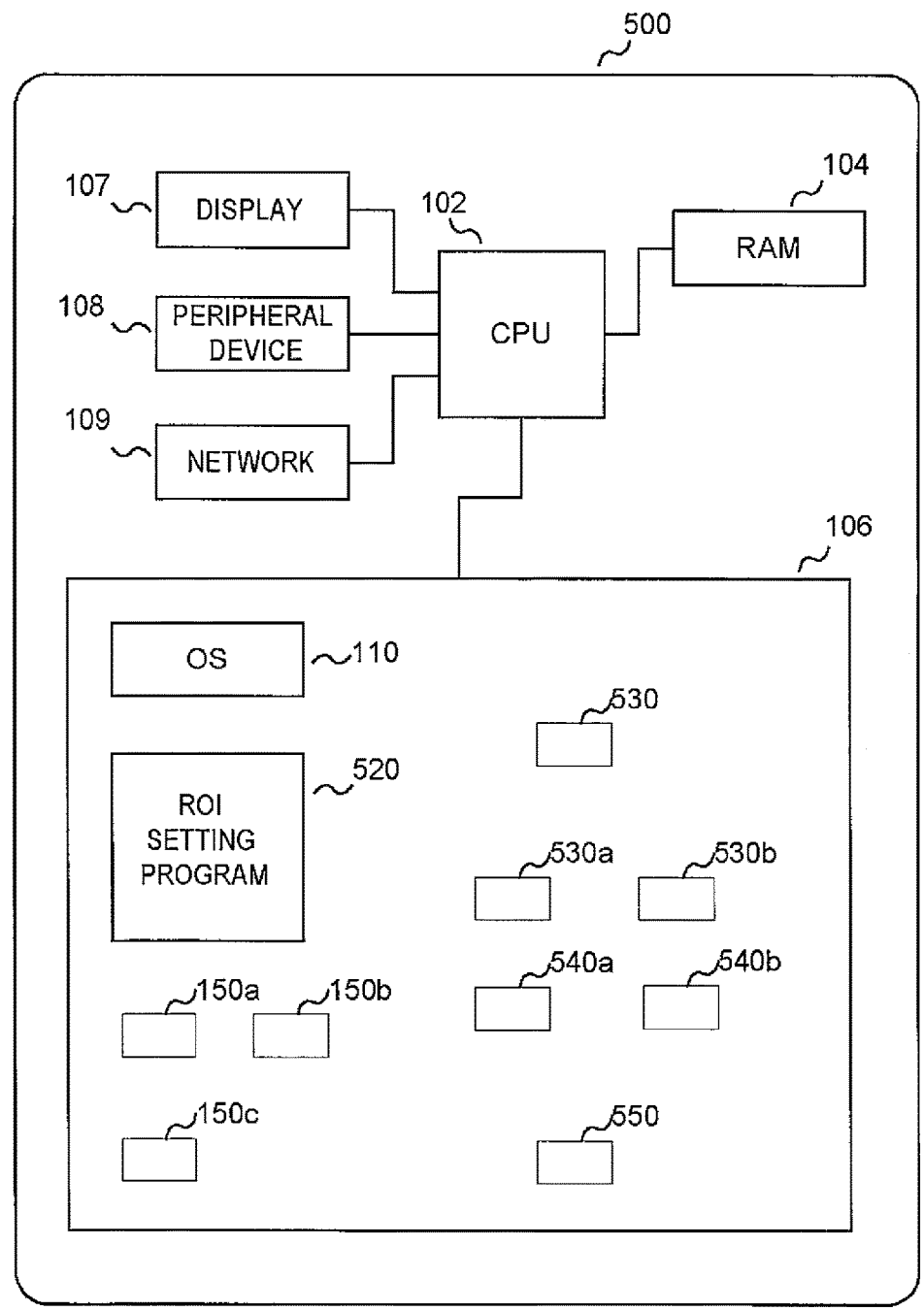
FIG. 5 is a diagram depicting a hardware configuration of a system for setting an ROI on an image of a living body.

A method for setting an ROI on an image of a living body, which is a second aspect of the technical ideas disclosed in the present application, will now be described with reference to FIG. 5 and the subsequent figures. FIG. 5 is a diagram showing main structures of a system 500, which is an example of hardware for carrying out processing for setting an ROI on an image of a living body. As shown in the figure, the hardware configuration of the system 500 is the same as that of the system 100 illustrated in FIG. 1, namely, the same as that of a general computer. Therefore, components identical to those in the system 100 are denoted with the same reference signs, and a description thereof will be omitted.

One of the features of the system 500 differing from those of the system 100 is that the system 500 has an ROI setting program 520. The ROI setting program 520 is provided with program instructions that, as a result of being executed by the CPU 102, cause the system 500 to execute the processing described later. Another feature of the system 500 is that it has three templates, including the positive template 150a, the negative template 150b, and the ROI template 150c. These three templates may be ones generated by the processing illustrated in FIG. 2. Depending on the embodiment, the program 520 and the templates 150a to 150c may be saved in the auxiliary storage device 106. Depending on the embodiment, these program and templates may be stored in an external device connect to the system 500 via, for example, a network.

The ROI setting program 520 is configured to cause the system 500 to execute processing for setting an ROI on image data 530 of a living body as a result of being executed by the CPU 102. The image data 530 of a living body can be a PET image generated for, for example, amyloid imaging. In other words, the image data 530 of a living body may be image data obtained by administering a radiopharmaceutical, such as $^{11}$C-PIB and $^{18}$F-Flutemetamol, to a subject and carrying out PET on the subject. As illustrated in FIG. 5, the image data 530 may be saved in, for example, the auxiliary storage device 106 or may be stored in an external device connected to the system 500 via, for example, a network.

Figure 6:
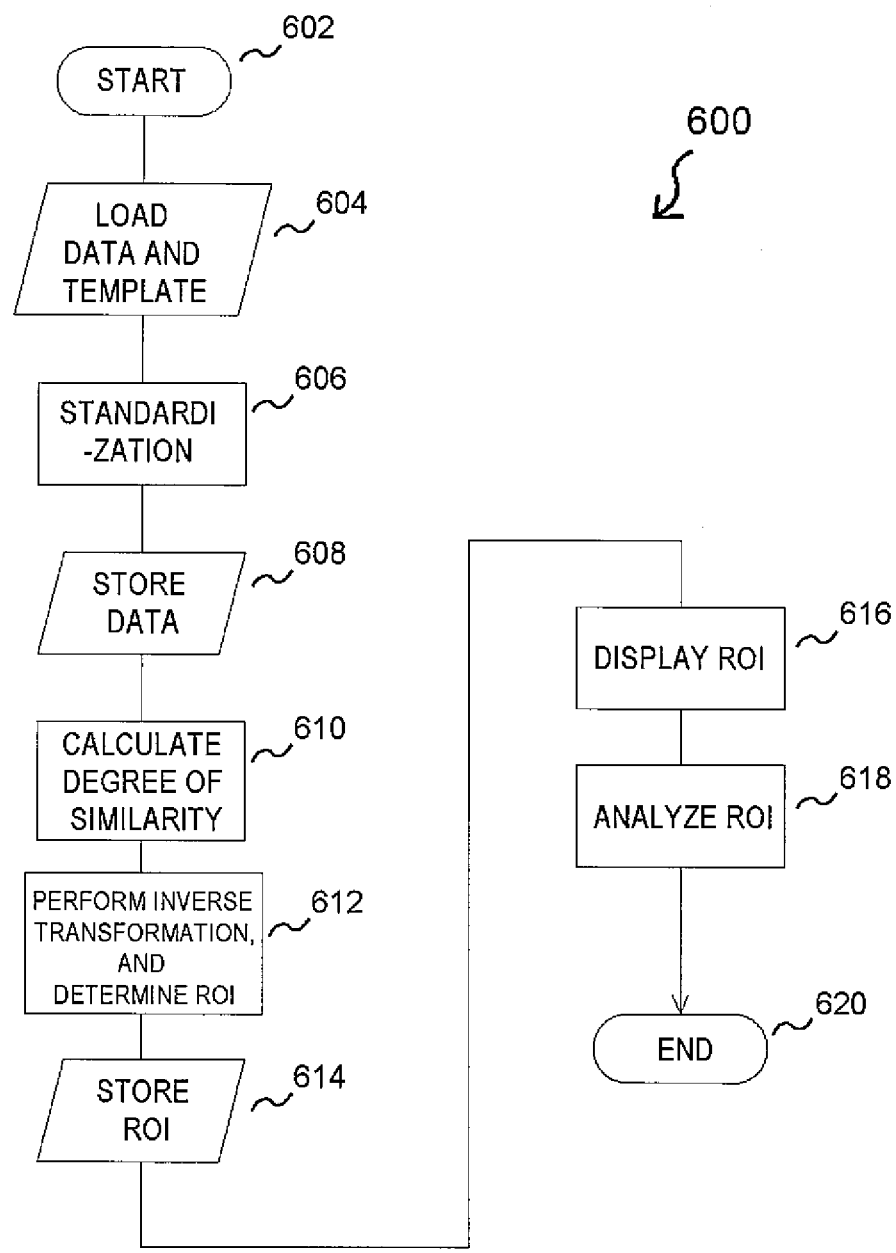
FIG. 6 is a diagram for describing a flow of an embodiment for setting an ROI on an image of a living body.

The flow of processing 600 carried out by the system 500 as a result of the ROI setting program 520 being executed by the CPU 102 will be described with reference to FIG. 6. Step 602 represents the start of the processing. In step 604, the positive template 150a, the negative template 150b, the ROI template 150c, and the PET image data 530 are loaded. In other words, these data are copied from the auxiliary storage device 106 to the main storage device 104. In step 606, the PET image data 530 is anatomically standardized with respect to each of the positive template 150a and the negative template 150b. In other words, the shape of the head image shown in the PET image data 530 is reshaped so as to match the shape of the positive template 150a or the negative template 150b. As described above, a program that can carry out such anatomical standardization processing is already available, and a program, such as the above-described PMOD and SPM, can be used.

In step 608, the image data and the transformation data after the end of the anatomical standardization processing in step 606 are stored for the subsequent processing. FIG. 5 illustrates, as image data 530a, the image data obtained as a result of applying anatomical standardization to the image data 530 with respect to the positive template 150a. In addition, data for transforming the image data 530 into the image data 530a is illustrated as transformation data 540a. Such transformation data can be represented, for example, in the shape of a matrix. Similarly, FIG. 5 illustrates, as image data 530b, the image data obtained as a result of applying anatomical standardization to the image data 530 with respect to the positive template 150b. In addition, data for transforming the image data 530 into the image data 530b (e.g., transformation matrix) is illustrated as transformation data 540b. Note that although the image data 530a and 530b, as well as the transformation data 540a and 540b, are illustrated as if stored in the auxiliary storage device 106, they may be often stored in the main storage device 104 in the case of a practical embodiment.

In step 610, the degree of similarity between the image data 530a that has undergone anatomical standardization by using the positive template 150a and the relevant positive template 150a is calculated. Furthermore, the degree of similarity between the image data 530b that has undergone anatomical standardization by using the negative template 150b and the relevant negative template 150b is calculated. This degree of similarity can be, for example, a cross-correlation coefficient. For example, a cross-correlation coefficient r between the image data 530a and the positive template 150a can be calculated as follows.

$$r = \frac{\sum_m \sum_n (A_{mn} - \overline{A})(B_{mn} - \overline{B})}{\sqrt{\left(\sum_m \sum_n (A_{mn} - \overline{A})^2\right)\left(\sum_m \sum_n (B_{mn} - \overline{B})^2\right)}}$$

Here, Amn represents the pixel value of a pixel mn of the image data 530a, and Bmn represents the pixel value of a pixel mn of the positive template 150a. Symbol A with an overline represents the mean pixel value of the image data 530a in a range in which a cross-correlation coefficient is calculated, and symbol B with an overline represents the mean pixel value of the positive template 150a in a range in which a cross-correlation coefficient is calculated.

Figure 7:
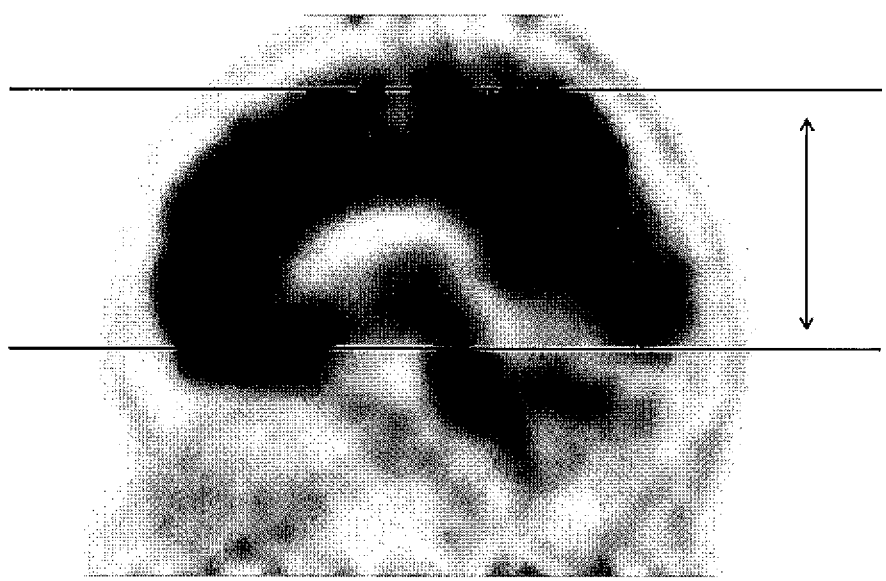
FIG. 7 is a diagram depicting an example of an area for calculating a cross-correlation coefficient.

Although the range in which the cross-correlation coefficient r is calculated may be the entire range of the image data 530a, the cross-correlation coefficient r may be calculated only in a partial range of the image data 530a, depending on the embodiment. As illustrated in, for example, FIG. 7, the cross-correlation coefficient may be calculated in the range from above the cerebellum to the parietal lobe. Furthermore, according to findings of the present inventors, calculating a cross-correlation coefficient in the range from above the cerebellum to the parietal lobe will bring about a more beneficial effect on determination of a final ROI, rather than in the entire range of the image data 530a. However, the range in which a cross-correlation coefficient is calculated is not limited to the range from above the cerebellum to the parietal lobe, and another range may be used.

A cross-correlation coefficient between the image data 530b and the negative template 150b can also be calculated in the same manner.

In step 612, it is determined which of the two cross-correlation coefficient values calculated in step 610 is higher. Then, inverse transformation of the transformation that has been carried out in step 606 is applied to the ROI template 150c, i.e., the transformation applied to the positive template 150a or the negative template 150b, whichever has the higher of the calculated cross-correlation coefficient values. By doing so, the ROI to be applied to the image data 530 is determined.

In other words, from among the two cross-correlation coefficients calculated in step 610, if, for example, the cross-correlation coefficient calculated between the image data 530a and the positive template 150a is higher, the transformation data 540a, which is transformation data used when the image data 530 is made to undergo anatomical standardization with respect to the positive template, is selected in step 612 from among the transformation data 540a and 540b that have been stored in step 608. Then, inverse transformation is obtained on the basis of this transformation data 540a, which was used when the image data 530 was anatomically standardized to the image data 530a. Then, this inverse transformation is applied to the ROI template 150c.

Conversely, from among the two cross-correlation coefficients calculated in step 610, if, for example, the cross-correlation coefficient calculated between the image data 530b and the negative template 150b is higher, the transformation data 540b, which is transformation data used when the image data 530 is made to undergo anatomical standardization with respect to the negative template, is selected in step 612. Then, inverse transformation is obtained on the basis of this transformation data 540b, which was used when the image data 530 was anatomically standardized to the image data 530b. Then, this inverse transformation is applied to the ROI template 150c.

Because this inverse transformation is applied, the ROI template is reshaped so as to match the brain shape in the image data 530. Therefore, if this reshaped ROI template is used, an ROI can be set on the image data 530 without reshaping the image data 530. The ROI template 150c that has been reshaped in this manner may be stored as ROI information 550 (step 614).

Figure 8:
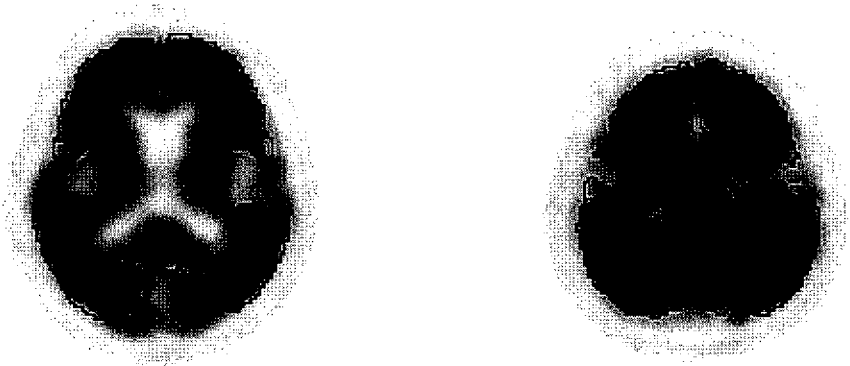
FIG. 8 is a diagram depicting an example of ROIs that have been determined according to an embodiment and that have been superimposed on cross-sectional images of example amyloid PET images.

FIG. 8 shows examples where ROIs determined in the above-described processing are superimposed on cross-sectional images of example amyloid PET images. The areas enclosed by a black solid line are the determined ROIs.

Figure 9:
FIG. 9 is a diagram depicting ROIs superimposed on the same cross-sectional images as in FIG. 8, wherein the ROIs have been set using MRI and an anatomical brain atlas.

For comparison with a conventional method, FIG. 9 shows a diagram resulting from superimposing ROIs that have been set using MRI and an anatomical brain atlas on the same cross-sectional images as those in FIG. 8. Also in FIG. 9, the areas enclosed by a black solid line represent ROIs. When the ROIs of FIG. 8 that have been set in the above-described embodiment are compared with the ROIs of FIG. 9 according to a conventional method, they considerably differ, such as the difference in the area extracted as an ROI in the vicinity of, for example, the visual cortex. Furthermore, in the ROIs of FIG. 9 that have been set according to a conventional method, there is an ROI that would be an obvious error, such as an ROI that is set in the scalp or the bone. These differences would have arisen from the fact that an ROI that is set by a conventional method is merely determined from anatomical knowledge, whereas the ROI that has been set in the above-described embodiment is an ROI determined on the basis of an actual nuclear medicine image. In other words, the above-described error has been caused probably because an ROI that is set by a conventional method does not include nuclear medical findings. It is needless to say that in setting an ROI on a nuclear medicine image, an ROI that is set according to an embodiment of the present application is more preferable.

In addition, an ROI according to a conventional method has a more detailed structure than necessary, compared with an ROI that has been set according to an embodiment of the present application, and not only requires many calculation resources for imaging analysis in the ROIs but also would be accompanied by a larger partial volume effect. Such a disadvantage occurs probably because an ROI according to a conventional method is set without taking into consideration the way the nuclear medicine imaging apparatus used detects radiation. An ROI that is set according to an embodiment of the present application would be more favorable than one that is set by a conventional method.

The following is a description of optional processing. In step 616 of FIG. 6, the ROI that has been set in step 612 may be superimposed for display on any cross section of the image data 530 to be analyzed. In addition, in step 618, some analysis may be carried out on the basis of the ROI that has been set. For example, the integration value or the mean value of the pixel values of pixels in the ROI may be calculated so that they can be displayed and output. By dividing the pixel value of each pixel of the image data by the mean value of the pixel values of pixels in an ROI on particular reference area (e.g., cerebellum) for the image data 530, the mean SUVR value in the ROI may be calculated, and, on the basis of this value, it may be automatically determined, for example, whether or not AD exists in the subject for whom the image data 530 for analysis has been generated. Step 620 indicates the end of the processing.

Figure 10:
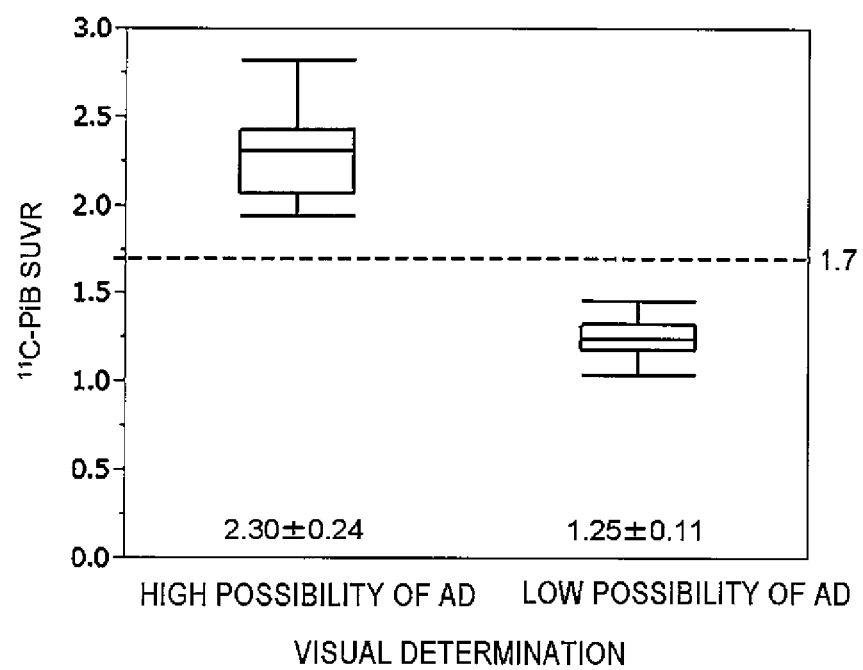
FIG. 10 is a diagram depicting the relationship between the result of automated determination as to whether the possibility of Alzheimer's disease being contracted is high or low by the use of an ROI determined according to an embodiment and manual determination by a richly-experienced physician.

In order to test the AD discriminating capability using an ROI that is set by the method according to the present application, an ROI was set on a total of 34 examples of AD and non-AD amyloid images by the method of the present application to calculate the mean SUVR in the ROIs. Results are shown in FIG. 10. As shown in FIG. 10, when the threshold of the SUVR was set to 1.7, it was possible to discriminate between an AD image (image of a subject considered to have Alzheimer's) and a non-AD image (image of a subject considered not to have Alzheimer's) at an accuracy level almost identical to that of visual evaluation by experienced physicians.

According to technical ideas disclosed in the present application, because it is possible to set an ROI for an imaging test of a living body without an MRI image, tests that are less burdensome to both the medical institution and the patients become possible. Furthermore, because an ROI is set on the basis of not anatomical information but functional information, a more suitable ROI can be set compared with ROIs that are set by a conventional method particularly in functional tests. Moreover, because it is possible to set an ROI on the original image, analysis can be carried out without changing pixel values of the original image. Technical ideas disclosed in the present application can be used for various medical imaging apparatuses, and can be used without being affected by the image quality or resolution.

Although the present invention has been described in detail by way of preferable embodiments, the above description and appended drawings have not been presented with the intention of limiting the scope of the present invention but have been presented to satisfy legal requirements. In addition to embodiments introduced above, many other variations of embodiments according to the present invention are available. For example, all the various types of numerical values shown in the description or on the drawings are just examples, and these numerical values are not intended to limit the scope of the invention. Individual features included in various types of embodiments introduced in the description or on the drawings are not ones that can be used only together with embodiments that are directly described to include those features but also can be used in combination with other embodiments described above, as well as with various types of embodiments that are not described. In particular, the order of processing introduced in the flowcharts does not necessarily need to be performed in the order described, but can be performed by changing the order according to preferences or necessity of the practitioner or can be performed concurrently, and furthermore, a plurality of blocks may be integrally implemented or may be implemented so as to be executed in the form of an appropriate loop. These variations are all included in the scope of the invention disclosed in the present application, and the scope of the invention is not limited by processing embodiments. The order of describing the processing identified in the claims does not necessarily identify the essential processing order, but, for example, embodiments with different processing orders, as well as embodiments in which processing including loops is executed, are included in the scope of the invention according to the claims. Irrespective of whether described or not in the current claims, the applicants claim that they have the rights to patent all forms of invention that do not depart from the spirit of the invention.

REFERENCE SIGNS LIST

100 System
102 CPU
104 Main storage device
106 Auxiliary storage device
107 Display interface
108 Peripheral device interface
109 Network interface
120 Positive/negative-template generation program
126 Template generation program
520 Setting program
530 Image data of living body

The invention claimed is:

1. A method for setting a Region of Interest (ROI) for an imaging test of a living body, the method comprising:
   performing first transformation for anatomically standardizing, with the use of a positive template, a nuclear medicine image acquired by applying a radiopharmaceutical to a subject;
   performing second transformation for anatomically standardizing the nuclear medicine image with the use of a negative template;
   calculating a degree of similarity between a first anatomical standardization image acquired by the first transformation and the positive template;
   calculating a degree of similarity between a second anatomical standardization image acquired by the second transformation and the negative template; and
   applying, to a ROI template, inverse transformation of the first transformation or the second transformation, whichever has the higher of the calculated degrees of similarity, in order to set the ROI.

2. The method according to claim 1,
   wherein the positive template is generated from nuclear medicine images of a plurality of subjects having a disease for which a nuclear medicine imaging test is conducted with the radiopharmaceutical,
   the negative template is generated from nuclear medicine images of a plurality of subjects not having the disease, and
   the ROI template is generated on the basis of a difference between the positive template and the negative template.

3. The method according to claim 1, wherein the imaging test is a test related to amyloid deposition.

4. The method according to claim 1, wherein the radiopharmaceutical is for amyloid imaging.

5. The method according to claim 1, wherein the degree of similarity is a cross-correlation coefficient.

6. A computer program provided with a program instruction configured to, when executed by a processing means of a system, cause the system to perform the method according to claim 1.

7. A system provided with a processing means and a storage means, wherein the storage means stores a program instruction, and the program instruction is configured to cause the system to perform the method according to claim 1 when executed by the processing means.

8. The system according to claim 7, wherein the program instruction is configured to, when executed by the processing means, cause the system to set an ROI on a nuclear medicine image on the basis of the ROI template to which the inverse transformation has been applied and to calculate and output a mean Standardized Uptake Value Ratio of the ROI set on the nuclear medicine image.

9. A method for setting a Region of Interest (ROI) for an imaging test of a living body, the method comprising:
   performing first transformation for anatomically standardizing, with the use of a positive template, a nuclear medicine image acquired by applying a radiopharmaceutical to a subject;
   performing second transformation for anatomically standardizing the nuclear medicine image with the use of a negative template;
   calculating a degree of similarity between a first anatomical standardization image acquired by the first transformation and the positive template;
   calculating a degree of similarity between a second anatomical standardization image acquired by the second transformation and the negative template; and
   setting the ROI by applying a ROI template to the first anatomical standardization image or the second anatomical standardization image, whichever has the higher of the calculated degrees of similarity.

10. The method according to claim 9,
    wherein the positive template is generated from nuclear medicine images of a plurality of subjects having a disease for which a nuclear medicine imaging test is conducted with the radiopharmaceutical,
    the negative template is generated from nuclear medicine images of a plurality of subjects not having the disease, and
    the ROI template is generated on the basis of a difference between the positive template and the negative template.

11. The method according to claim 9, wherein the imaging test is a test related to amyloid deposition.

12. The method according to claim 9, wherein the radiopharmaceutical is for amyloid imaging.

13. The method according to claim 9, wherein the degree of similarity is a cross-correlation coefficient.

14. A computer program provided with a program instruction configured to, when executed by a processing means of a system, cause the system to perform the method according to claim 9.

15. A system provided with a processing means and a storage means, wherein the storage means stores a program instruction, and the program instruction is configured to cause the system to perform the method according to claim 9 when executed by the processing means.

16. The system according to claim 15, wherein the program instruction is configured to, when executed by the processing means, cause the system to set an ROI on a nuclear medicine image on the basis of the ROI template to which the inverse transformation has been applied and to calculate and output a mean Standardized Uptake Value Ratio of the ROI set on the nuclear medicine image.

* * * * *